United States Patent [19]

Scholz et al.

[11] Patent Number: 5,273,802

[45] Date of Patent: Dec. 28, 1993

[54] ORTHOPEDIC CASTING MATERIALS HAVING SUPERIOR LAMINATION CHARACTERISTICS DUE TO NAPPED SURFACE

[75] Inventors: Matthew T. Scholz; Ralph A. Wilkens; Robert L. Assell; Charles E. Alexson, all of St. Paul, Minn.

[73] Assignee: Minnesota Mining and Manufacturing Company, St. Paul, Minn.

[21] Appl. No.: 376,873

[22] Filed: Jul. 7, 1989

[51] Int. Cl.$^5$ .................. A61F 5/04; A61L 15/00; B32B 3/02; A61B 17/06

[52] U.S. Cl. .................. 428/76; 428/85; 428/86; 428/91; 428/92; 428/96; 428/245; 428/253; 428/254; 428/260; 428/273; 602/3; 602/8; 602/41; 602/44; 206/438

[58] Field of Search ........... 428/253, 254, 85, 95, 428/96, 156, 255, 273, 272, 290, 76, 86, 91, 92, 245, 260; 128/90, 155, 156; 156/583.5; 602/1, 3, 6, 8, 41, 44

[56] References Cited

U.S. PATENT DOCUMENTS

| | | | |
|---|---|---|---|
| 3,506,479 | 4/1970 | Breens et al. | 428/96 |
| 3,542,632 | 11/1970 | Eickhoff | 428/85 |
| 3,881,473 | 5/1975 | Corvi et al. | 128/156 |
| 4,081,582 | 3/1978 | Butterworth et al. | 428/284 |
| 4,260,445 | 4/1981 | Mayuni et al. | 156/276 |
| 4,316,457 | 2/1982 | Liegeois | 128/156 |
| 4,333,976 | 6/1982 | Okamoto et al. | 428/266 |
| 4,376,438 | 5/1983 | Straube et al. | 128/90 |
| 4,411,262 | 10/1983 | von Bonin et al. | 128/90 |
| 4,502,479 | 5/1985 | Garwood et al. | 128/90 |
| 4,609,578 | 9/1986 | Reed | 428/76 |
| 4,667,661 | 5/1987 | Scholz et al. | 128/90 |
| 4,705,840 | 11/1987 | Buckanin | 528/53 |
| 4,741,941 | 5/1988 | Englebert et al. | 428/71 |
| 4,774,937 | 10/1988 | Scholz et al. | 128/90 |
| 4,841,958 | 6/1989 | Ersfeld et al. | 128/90 |
| 4,856,502 | 8/1989 | Ersfeld et al. | 128/90 |
| 4,923,555 | 5/1990 | Elliot et al. | 156/583.5 |

FOREIGN PATENT DOCUMENTS 0290207 4/1988 European Pat. Off.

OTHER PUBLICATIONS

"Scotchflex TM Conformable Casting Tape"—product brochure of the Orthopedics Product Division of 3M, St. Paul, Minn.

"CaraGlas ®—A New Generation in Casting Technology"—product brochure of Carapace Incorporated, Tulsa, Okla.

Primary Examiner—George F. Lesmes
Assistant Examiner—James D. Withers
Attorney, Agent, or Firm—Gary L. Griswold; Walter N. Kirn; Dale E. Hulse

[57] ABSTRACT

The present invention relates to novel orthopedic casting materials having superior layer to layer lamination, and methods for preparing the same. The orthopedic casting materials comprise a resin-coated scrim having a plurality of projections along at least one surface thereof. Preferably, each projection comprises a bundle of at least about 8 filaments, and the scrim has from about 75 to about 1500 projections per gram of scrim. The projections serve to mechanically interact with adjacent layers of the material, thereby significantly enhancing the lamination properties of the resultant material and resisting delamination once the material has cured.

35 Claims, 6 Drawing Sheets

ORTHOPEDIC CASTING MATERIALS HAVING SUPERIOR LAMINATION CHARACTERISTICS DUE TO NAPPED SURFACE

BACKGROUND

1. The Field of the Invention

The present invention relates to novel orthopedic casting materials, and in particular, to orthopedic casting materials which are formulated so as to have improved lamination between adjacent layers of the materials.

2. The Prior Art

Many different orthopedic casting materials have been developed for use in the immobilization of broken or otherwise injured body parts. Some of the first casting materials developed for this purpose involve the use of plaster of Paris bandages.

More recently, polyurethane prepolymers were found to be extremely useful in formulating a resin for orthopedic casting materials, as disclosed, for example, in U.S. Pat. No. 4,502,479 (Garwood et al.), U.S. Pat. No. 4,609,578 (Reed), U.S. Pat. No. 4,667,661 (Scholz et al.), and U.S. Pat. No. 4,774,937 (Scholz et al.). Most commonly, a knitted fiberglass fabric is used as the scrim onto which such polyurethane prepolymers are coated.

In the quest for an improved orthopedic casting material, those skilled in the art recognize that effective layer to layer lamination of the orthopedic casting material upon application and after cure is of the utmost importance. One way to increase the lamination properties of a polyurethane prepolymer based orthopedic casting material would be to increase the proportion of the "soft component" primarily responsible for adhesion (e.g., the polyol) to the "hard component" primarily responsible for rigidity (e.g., the isocyanate) in the formulation of the polyurethane prepolymer. Unfortunately, however, although increasing the relative proportion of the soft component generally does result in better adhesion or lamination, the rigidity or strength of the resultant cast is significantly decreased due to the corresponding decrease in the proportion of the hard component. Thus, a compromise must be made between the relative proportions of hard and soft components employed in the resin so as to provide a balance between the properties of strength and lamination in the formulated casting material.

Another approach to increasing the lamination characteristics of an orthopedic casting material is to increase the amount of resin coated onto or impregnated into the scrim. However, increased resin loading often results in resin migration and/or pooling of the resin during storage. This is undesirable not only from the standpoint of losing the resin from the scrim during significant storage periods, but also, such resin migration results in uneven distribution of the resin on the scrim. Such uneven distribution of the resin can adversely affect the handling properties of the material upon application as well as the uniformity of the finished cured cast with regard to such characteristics as resistance to delamination, porosity, and compression strength, etc. Moreover, increased resin loading often decreases the air porosity of the resultant material, and adequate porosity is an important characteristic of orthopedic casting materials.

From the foregoing, it will be appreciated that what is needed in the art is an improved orthopedic casting material which has enhanced lamination properties without the necessity of changing the resin composition. It would be a further advancement in the art to provide orthopedic casting materials which have such enhanced lamination properties without employing increased amounts of resin in the scrim and without decreasing the porosity of the materials. Such orthopedic casting materials and methods for preparing the same are disclosed and claimed herein.

BRIEF SUMMARY AND OBJECTS OF THE INVENTION

The present invention relates to orthopedic casting materials which have surprisingly enhanced lamination properties without changing the resin composition and without the necessity of using increased amounts of resin. The present invention achieves such enhanced lamination properties by the formation of projections which extend from the surface of the resin-coated casting material, preferably in a substantially perpendicular fashion.

The scrim employed is preferably a knitted fabric made, for example, of fiberglass, and is coated with a curable resin, such as a water curable, isocyanate functional, polyurethane prepolymer. The aforementioned projections are formed along at least one side of the scrim, preferably before the scrim is coated with the curable resin. Such projections serve to mechanically interact with adjacent layers of the resin-coated orthopedic casting material upon application, and become mechanically entangled with such adjacent layers so as to increase the lamination between the adjacent layers.

Because the present invention achieves enhanced lamination by the mechanical interaction between adjacent layers rather than by changing the chemical composition of the curable resin, enhanced lamination can be achieved without decreasing the amount of hard component in the resin which is responsible for strength. Moreover, such mechanical bonding achieved by the projections of the scrims of the present invention does not require the use of increased amounts of resin. In fact, because of the enhanced lamination provided by the resin-coated scrims of the present invention, lesser amounts of resin or resins with a higher proportion of hard component can be employed in the present invention to achieve lamination equivalent to that achieved in orthopedic casting materials presently available in the art.

It is therefore believed that the projections along the scrims of the present invention must be capable of mechanical interaction or interlocking between adjacent layers of the resultant orthopedic casting material and must be in sufficient population in order to achieve enhanced lamination. By varying the physical characteristics of the projections and the population of projections along the scrim, the degree of laminatability can be controlled as desired.

The present invention also relates to a method for forming such orthopedic casting materials having projections to enhance lamination between adjacent layers. In one presently preferred embodiment, the scrim material (before resin coating) is passed between two rollers, one of which is a knurled roller having teeth which abrade the material so as to break at least a portion of certain yarns of the material, and thereby form the projections. The scrim material is then preferably passed over itself to encourage the projections to stand up and away from the surface of the scrim material.

It is, therefore, an object of the present invention to provide orthopedic casting materials involving a curable resin which exhibit improved lamination properties, while at the same time do not require increased proportions of soft component in the resin and do not require the use of additional amounts of resin.

Another object of the present invention is to provide methods for making such orthopedic casting materials having enhanced lamination properties.

These and other objects and features of the present invention will become more fully apparent from the following description and appended claims, taken in conjunction with the accompanying drawings.

BRIEF DESCRIPTION OF THE DRAWINGS

In the following photographic FIGS. 1A-1H, various fiberglass yarns or tapes are shown without any resin thereon. It will be understood that each of the fiberglass yarns or tapes which are the subject of photographic FIGS. 1A-1H were coated with resin at one time, but the resin was removed prior to the taking of photographic FIGS. 1A-1H. In each of FIGS. 1A-1H, resin removal was accomplished by gently swirling the subject material in a solution of 50% methanol/50% tetrahydrofuran (percent by volume). Care was taken to ensure that each subject fabric did not rub over itself and cause further abrading. The subject tape was then removed, and the process repeated in a fresh mixture of solvent. Finally, each tape sample was dried by suspending it in air under a ventilated hood.

DETAILED DESCRIPTION OF THE PREFERRED EMBODIMENTS

Figure 1A:
FIG. 1A is a photographic representation (taken at 10×magnification) of an unabraded fiberglass yarn (ECG-75 1/0 0.7Z, available from Owens-Corning Fiberglass), formerly part of a chain stitch, which was removed from a heat cleaned and heat-set, knitted fiberglass scrim. (This scrim was knit into the same pattern as the scrim used in 3M's Scotchcast® 2 and Scotchcast® Plus products (this scrim being referred to at 3M as the "Scotchcast® 2 scrim"), only using the ECG fiberglass yarn referenced above rather than the ECDE fiberglass yarn used in 3M's Scotchcast® 2 scrim, the ECG fiberglass yarn having thicker filaments than the ECDE fiberglass yarn.)
Figure 1B:
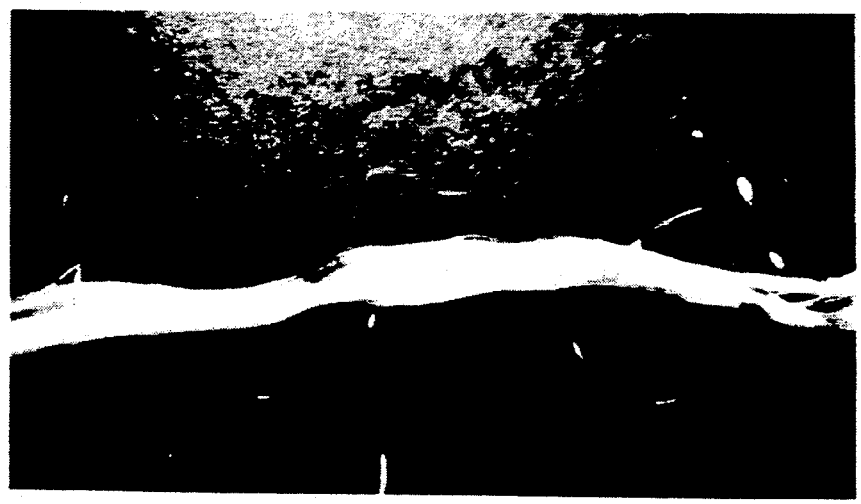
FIG. 1B is a photographic representation (taken at 10×magnification) of the yarn of FIG. 1A, held with the minimum amount of tension needed to straighten it.
Figure 1C:
FIG. 1C is a photographic representation (taken at 10×magnification) of the same type of fiberglass yarn as shown in FIG. 1A, except that the fiberglass yarn of this FIG. 1C has been abraded in accordance with the method schematically outlined in FIG. 4 below, using a force of 450 newtons between the knurled roller and the motor driven roller. In this regard, one or more projections within the scope of the present invention may be viewed along the abraded yarn of this FIG. 1C.
Figure 1D:
FIG. 1D is a photographic representation (taken at 10×magnification) of the fiberglass yarn of FIG. 1C, held with the minimum amount of tension needed to straighten it.
Figure 1E:
FIG. 1E is a photographic representation (taken at 10×magnification) of the same type of fiberglass yarn as shown in FIG. 1A, with the exception that the fiberglass yarn of this FIG. 1E has been abraded in accordance with the method schematically set forth in FIG. 4 below (using a force of 750 newtons between the knurled roller and the motor driven roller) to form projections within the scope of the present invention. The projections noted in this FIG. 1E are more numerous and somewhat more random in configuration.
Figure 1F:
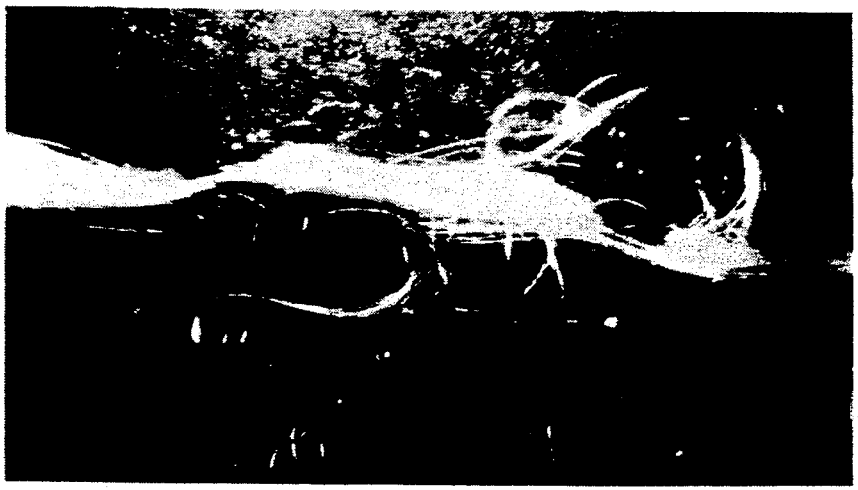
FIG. 1F is a photographic representation (taken at 10×magnification) of the fiberglass yarn of FIG. 1E, held with the minimum amount of tension needed to straighten it.
Figure 1G:
FIG. 1G is a photographic representation (taken at 20×magnification) of projections along the surface of the same type of knitted fiberglass scrim from which the yarn of FIG. 1A was removed. This fiberglass scrim was also abraded in accordance with the method of FIG. 4, using a force of 750 newtons between the knurled roller and the motor driven roller. For purposes of this photographic FIG. 1G, the abraded fiberglass scrim was bent (in the machine direction) around the edge of a piece of cardboard (having a thickness of 1 mm) under a tension of about 37.5 grams per centimeter of width in order to more carefully view the projections of the scrim extending from that edge.
Figure 1H:
FIG. 1H is a photographic representation (taken at 20×magnification) of projections along the surface of the same type of knitted fiberglass scrim from which the yarn of FIG. 1A was removed. This fiberglass scrim was also abraded in accordance with the method of FIG. 4, using a force of 450 newtons between the knurled roller and the motor driven roller. For purposes of this photographic FIG. 1H, the abraded fiberglass scrim was bent (in the machine direction) around the edge of a piece of cardboard (having a thickness of 1 mm) under a tension of about 37.5 grams per centimeter of width in order to more carefully view the projections of the scrim extending from that edge.

The present invention relates to resin-coated materials which have enhanced lamination properties. These resin-coated materials have particular utility as orthopedic casting materials, however, such is not their only utility. Hence, although the following discussion of the resin-coated materials of the present invention is set forth in the context of an orthopedic casting material application, it will be appreciated that the applications and uses of the materials of the present invention are not so limited, and a few of the other utilities of the present invention will be noted hereinafter.

One of the discoveries made in connection with the present invention is that projections may be formed along a scrim to be coated with resin, which projections are capable of mechanically interacting with adjacent layers of the resin-coated scrim upon application to increase and substantially enhance lamination. Of course, the resin coated onto the scrim is also responsible for some of the lamination achieved between adjacent layers. However, when using the same degree of resin loading, it has been discovered that much better lamination can be achieved by providing projections along the resin-coated scrim versus utilizing a scrim having no such projections.

In understanding the scope of the present invention, it is important that the term "projections", as used herein, be more carefully defined. A "projection", as used herein, shall refer to a portion of the scrim which extends substantially outwardly from the plane defined by the flat scrim, which extension is physically capable of mechanically interlocking, bonding, entangling, engaging, or otherwise mechanically interacting with another layer of the scrim in such a way as to mechanically enhance lamination between the layers of the scrim.

In connection with the foregoing, it is noted that, in many fabric materials used as orthopedic scrims, stray "hairs" or fibers may extend from the surface of the fabric scrim. However, as a general rule, such stray fibers do not have the physical properties necessary to measurably enhance lamination, and therefore do not qualify as "projections" as are needed in the successful practice of the present invention. As will be appreciated, each "projection" within the scope of the present invention actually comprises a bundle of filaments or fibers. The physical characteristics of a particular bundle of fibers will determine whether or not such a bundle can properly function as a "projection" within the scope of the present invention to enhance lamination. In order to more carefully define the invention over the prior art, applicants have considered suitable projections within the scope of the present invention to be only those scrim extensions, as defined hereinabove, which comprise a bundle of 8 or more filaments.

Although it is somewhat difficult to define a minimum number of filaments per bundle which will provide the strength and other physical characteristics necessary to provide a projection which will enhance lamination in accordance with the present invention, it has been found that generally those scrim extensions having much less than 8 filaments per bundle do not significantly enhance lamination. Hence, applicants have chosen to define their projections as those extensions which comprise a bundle of 8 or more filaments or fibers.

Preferably, the projections of the present invention extend in a substantially perpendicular direction from the plane defined by the scrim. However, as seen in the photographic figures included herein, the projections quite often also have curved ends. Also preferably, most of the filaments in the bundle of a particular projection are relatively close together and are oriented in substantially the same direction. However, it will be understood that those bundles having filaments going in various directions can still qualify as a "projection" within the scope of the present invention where sufficient mechanical interaction is provided to enhance lamination, and such more randomly distributed projections have indeed been observed to function satisfactorily. In the case of such a projection where the fibers are somewhat more random in direction, the term "projection" refers to that group of filaments which originate at substantially the same site along a yarn (even though the ends of some of the filaments may point in different directions), and not to filaments originating at a plurality of different sites along a yarn as may be the case with stray fibers along the scrims of the prior art.

The fabric sheets or scrims of the present invention are preferably fabricated from knitted or woven materials. In this regard, the presently preferred scrim material for practicing the present invention is a knitted fiberglass material. The presently most preferred scrim material is a highly extensible, heat-set, knitted fiberglass scrim which is set forth in U.S. Pat. No. 4,609,578 (Reed), which patent is incorporated herein by reference, one example of which is known by 3M, St. Paul, Minn., as the Scotchcast ® 2 knitted fiberglass scrim. The Scotchcast ® 2 scrim is used in the manufacture of 3M's Scotchcast ® 2 and Scotchcast ® Plus orthopedic casting materials.

The presently most preferred scrims of the present invention use the same knit pattern as the Scotchcast ® 2 scrim, but can employ a yarn having filaments of a different diameter (e.g., larger diameter) if desired. The Scotchcast ® 2 scrim is a 2 bar, 18 gauge Raschel warp knit construction wherein the front bar executes an open chain stitch, the back bar lays in across 4 needles, and the pattern notation is 2-0,0-2 and 0-0, 8-8 for the front and back bars, respectively.

It will be appreciated that, although fiberglass is presently preferred, other materials may be used to formulate the scrims of the present invention such as polyolefins, polyesters, polyamides, cotton, and other natural fibers, either alone or mixed with fiberglass as a blend. Again, the important criteria in choosing a material for formulating the scrim is that projections can be formed out of the scrim material which will have the necessary characteristics to provide enhanced lamination by mechanical interaction in accordance with the teachings of the present invention, and that the resultant scrim will have the strength, porosity, and durability required for an orthopedic casting material.

In accordance with the teachings of U.S. Pat. No. 4,609,578, the presently preferred highly extensible, heat-set, knitted fiberglass scrim is prepared as follows.

It is preferred to start with knitted fiberglass fabric which exhibits at least about 22–25%, and preferably greater than 35% extensibility in the lengthwise direction. To determine extensibility, the following method is employed. A length of fiberglass tape (upon which a 10 inch (25.4 cm) section has been marked) is placed in the 1"×5"×¼" grips of a standard "Instron" Tensile Tester, with the grips spaced 10 inches (25.4 cm) apart, and a load of 5 pounds (2.3 kg) is applied. The length of the fabric in the stretched position is compared to its length in the unstretched state to determine extensibility. A load of 5 pounds (2.3 kg) was selected as this approximates the maximum tension typically used when applying an orthopedic casting tape.

Knitted fiberglass fabrics meeting the initial extensibility requirements are known. Fiberglass knitted fabrics with good extensibility are achievable with two common knitting methods: Raschel and tricot. Extensible two and three bar Raschel knits can be produced by regulating the amount of yarn in each stitch. Factors which affect the extensibility of fiberglass Raschel knits are the size of the loops in the chain stitch, especially in relation to the diameter(s) of the yarn(s) which passes through them, and the amount of loose yarn in the layin stitches. If a chain loop is formed and two strands of layin yarn pass through it which nearly fill the loop, then the loop cannot be deformed or elongated, and little or no stretch will be observed. Conversely, if the layin yarns do not fill the loop, then application of tension will deform the loop to the limits of the layin yarn diameter and stretch will be observed. Therefore, the larger the chain loop relative to yarn diameter, the greater the stretch. Similarly, the amount of yarn in the layin stitch in excess of that needed to lock the chain rows together is proportional to the imparted stretch. Tricot knits usually result in greater extensibility because their construction allows the openings in the fabric to deform. Typically, as these fabrics are extended in one direction, the fabric narrows in the perpendicular direction. Another basic type of knitting which results in stretchy fabrics is generally called tubular knitting which is commonly employed to knit socks, orthopedic stockinet, etc. A fabric called "Tubular Weave Stockinette" distributed by Otto Bach Orthopedic Industries, Inc, Minneapolis, Minn., is a fiberglass fabric, knit by a Raschel machine, and exhibits approximately 50% extensibility in the crosswise direction and approximately 175% extensibility in the lengthwise direction.

For orthopedic casting materials, the fiberglass fabric selected, in addition to having the extensibility requirements noted above, should be of a suitable thickness and mesh size to ensure good penetration of the curing agent (such as water in the case of a water curable resin-coated material) into the roll of resin-coated tape and to provide a finished cast with adequate strength and porosity. Such fabric parameters are well-known to those skilled in the art and are described in U.S. Pat. No. 4,502,479 (Garwood et al.), which patent is incorporated herein by reference.

In processing preferred knitted fiberglass fabrics of the present invention, a length of fabric is heat-set essentially without tension. Preferably, the fabric is wound onto a cylindrical core so large batches can be processed at one time in a single oven. Care must be taken to avoid applying undue tension to the fabric which would distort the knots and loops. To prevent applying tension to the fabric during winding, the winding operation must be performed with a sag in the fabric as it is wound on the core.

A continuous heat-setting process may also be used in which a length of fabric is placed without undue tension on a moving conveyor system and passed through an oven for sufficient time and temperature to achieve heat-setting of the fabric.

The heat-setting step may be performed in a number of conventional ways known to the art, and is preferably done at a temperature and for a period of time which is also sufficient to remove the sizing from the fabric. (Sizing is a substance, for example, starch oil, which is applied to facilitate the knitting process.) Heat-setting and desizing is generally carried out by heating the fabric in a batch convection oven at a temperature in the range of about 350° to about 550° C., preferably from about 400° C. to about 450° C. for a period of from about 6 hours to about 9 hours. It is presently preferred that the heat-setting and desizing step be carried out in the oven for a time sufficient to remove as much of the sizing as possible and to heat-set the fabric tape to a point that significant fraying will not be experienced when the fabric is cut. In this regard, it is generally desirable to remove at least 75% of the sizing, and more preferably, at least 90% or more of the sizing. Other desizing methods such as solvent extraction or enzymatic degradation may also be employed. In this regard, some typical chemical desizing processes are described in U.S. Pat. Nos. 3,686,725; 3,787,272; and 3,793,686.

Preferably, the modulus of elasticity of the material forming the scrims of the present invention is from about 5 to about 150 gigapascals. In the case of fiberglass, the modulus of elasticity is preferably from about 10 to about 100 gigapascals. The average tensile strength of the individual yarns in the knitted fabrics of the present invention is preferably from about 1 to about 2.5 gigapascals when measured at a temperature of 72° F. (22° C.) and under an atmosphere of 50% relative humidity. In the case of fiberglass, the yarns have an average tensile strength of from about 1 to about 2.5 gigapascals when measured at a temperature of 72° F. (22° C.) and under an atmosphere of 50% relative humidity.

The fabric scrims or sheets of the present invention also preferably have a basis weight of from about 0.010 to about 0.075 g/cm$^2$. Useful fiberglass scrims typically have a basis weight of from about 0.005 g/cm$^2$ to about 0.075 g/cm$^2$.

Fiberglass yarns which are useful in the manufacture of the fabric scrims of the present invention are typically multifilament yarns. Monofilament yarns are believed to be less useful, since scrims formed therefrom are typically not capable of holding as much curable resin and since they would not provide projecting bundles of filaments as projections but rather, single filaments. As evidenced by the yarns employed in U.S. Pat. No. 4,609,578 (Reed), the use of multifilament fiberglass yarns to provide fiberglass fabrics is well known to those skilled in the art. These multifilament yarns are generally manufactured from many very tiny filaments, e.g., from about 52 to about 2000 filaments or more per yarn.

After a suitable scrim has been formed, such as the knitted fiberglass scrims described herein, the scrim is next treated to form projections on at least one surface thereof. This is accomplished by a controlled breaking of at least a portion of the filaments in some of the yarns on at least one side of the scrim. It should be noted that, although in practicing the present invention projections may be formed on both sides of the scrim, such is typically not necessary. Hence, it is presently preferred to form projections on only one side of the scrim. In this regard, it is presently preferred to abrade the technical face of the knitted scrim (which, in the preferred Scotchcast ® 2 scrim, is the side of the scrim where the chain stitches are more exposed than the layin yarns), thereby forming the projections on that side of the scrim.

The projections may be formed by any one of a number of techniques which provide the degree of yarn stitch breakage desired. For example, the fabric scrim may be passed over one or more sharp or blunt teeth or blades so as to abrade or cut the surface of the scrim and break certain yarns to the degree required. Alternatively, sharp teeth or blunt teeth can be brought into contact with the fabric rather than passing the fabric over the same. Hence, it will be appreciated that such breakage can be accomplished in either a continuous or intermittent process. In one process, an array of blunt or sharp teeth is thrust intermittently against a belt of fabric scrim carried on or past a hard surface so as to abrade the fabric and cause the yarn breakage as desired.

By way of another example, abrasive wheels and brushes may be used to contact the fabric scrim and provide the abrasion and yarn breakage desired. The presently preferred abrasive wheels which may be used for this purpose include the 244E three-M-ite ® resin bonded cloth PGC ® wheel (available from 3M, St.

Paul, Minn.), sandpaper composite wheels and Scotchbrite® brand finishing flap brush 7S SFN abrasive wheels (also available from 3M).

The presently most preferred method for forming the projections of the present invention, however, involves passing the fabric scrim between a first smooth roller (such as a rubber or metal roller) and a second knurled roller. The first smooth roller is the drive roller, and may have, for example, a neoprene elastomer coated surface with a durometer hardness of 70±5 units so as to provide a hard, smooth, wear resistant surface. The second knurled roller is the idler roller and may have either a straight or patterned knurl, but the presently most preferred knurled roller has a straight knurl and sharp teeth thereon (sometimes called a "splined" roller).

Preferably, after being abraded by the knurled roller so as to break the yarns to the desired degree, the abraded surface of the scrim is passed over itself so as to encourage the projections to stand up and away from the surface of the fabric scrim. Alternatively, the abraded scrim could be passed over a knife blade or other object to encourage the projections to stand up.

Advantageously, the amount of abrasion and hence the number and size of projections produced by the above-described process may be carefully regulated by adjusting the force between the two rollers. Increasing the force between the rollers increases the number of projections formed, and hence increases the lamination properties of the resultant material by as much as 50% to 100% or more. Too much pressure, however, may result in so much abrasion that the integrity of the scrim is compromised. Thus, for purposes of the present invention, the force between the smooth roller and knurled roller is generally kept within the range from about 150 newtons to about 750 newtons, preferably within the range from about 300 newtons to about 600 newtons, when using the presently preferred straight knurled roller dimensions and geometry disclosed hereinbelow, which preferred knurled roller was used in each of the examples included herein where reference is made to a "knurled roller".

Another technique which may be used to control the amount of breakage of the yarn stitches, and hence the number and size of projections formed, is by regulating the number, size, and shape of the knurls on the knurled roller. The knurls on the presently preferred straight knurled roller are about 0.15 centimeters high, are spaced to provide about 4.7 teeth per centimeter, and have a triangular shape. These knurls extend in a regular pattern across the entire roller, which is about 17.5 centimeters long and about 7.5 centimeters in diameter. (It should be noted that the ranges and values for the force between the knurled and smooth rollers set forth herein are based upon a knurled roller having the foregoing dimensions and geometry. For knurled rollers having different dimensions or geometries, it might be necessary to adjust these force values somewhat to ensure that the proper abrasion is achieved without significantly compromising the integrity of the scrim.) However, knurls which are of other geometric configurations (such as patterned straight knurls) or having teeth in the shape of diamonds or other configurations can also be employed. Moreover, patterned rolls useful for abrading the scrims of the present invention could also be made by processes other than knurling, such as etching, machining, engraving, laser cutting, electric discharge machining, and the like.

In a presently preferred embodiment of the present invention, from about 0.5% to about 50% of the filaments are broken in those yarns from which the projections are formed, most preferably from about 1% to about 10% of the filaments are broken. However, it will be understood that it is also possible to break all of the filaments in an entire yarn to provide a projection within the scope of the present invention. In such an instance, the yarns broken should be spaced apart such that, after completely severing the selected yarns, the integrity of the scrim is not undesirably compromised.

As mentioned previously, each projection formed within the scope of the present invention comprises a bundle of at least about 8 filaments. In one presently preferred embodiment of the present invention, the projections comprise bundles of from about 8 to about 200 filaments on the average, preferably from about 8 to about 100 filaments on the average. Again, the important criteria is that the projections have adequate strength to achieve the mechanical interaction necessary to increase the lamination characteristics of the resultant material.

The number or population of projections per unit area of the scrim should also be controlled. In this regard, it is presently preferable to form the fabric scrim such that it has from about 1 to about 50 projections per square centimeter, preferably from about 5 to about 35 projections per square centimeter.

Because, however, some orthopedic casting scrims are more open (i.e., utilize less material and/or have larger openings) than other orthopedic scrims, the desired population of projections is best thought of in terms of projections per unit weight of scrim rather than per unit area. Hence, in a lightweight scrim which is more open, fewer projections will be needed to provide the same projections/unit weight of fabric scrim than a scrim that is heavier and not as open. In this regard, the fabric scrims of the present invention preferably have from about 75 to about 1500 projections per gram of fabric scrim on the average, more preferably from about 100 to about 1000 projections per gram of fabric scrim, and most preferably from about 300 to about 700 projections per gram of fabric scrim.

Although the projections of the present invention may be of varying length, the presently preferred average length of the projections is from about 0.1 to about 16 millimeters, more preferably from about 0.1 to about 8 millimeters. Similarly, when the projections comprise filaments which point substantially in the same direction, the presently preferred average diameter of the projections of the present invention is from about 0.035 to about 2 millimeters, and more preferably from about 0.1 to about 1 millimeter.

Once the fabric scrim has been prepared and the appropriate projections have been formed thereon, the scrim is then coated or impregnated with a curable resin. Many techniques for achieving such resin coating or impregnation are well known to those skilled in the art.

The presently preferred curable resins used to coat the scrims of the present invention are water curable resins. In this regard, water curable, isocyanate functional, polyurethane prepolymers are presently most preferred.

Presently preferred resins for use in the present invention include those disclosed in U.S. Pat. No. 4,667,661 (Scholz et al.) and U.S. Pat. No. 4,774,937 (Scholz et al.), which patents are incorporated herein by reference. The resins disclosed in the two aforementioned patents include tack reducing agents which facilitate application of the orthopedic casting materials.

However, in one presently preferred embodiment of the present invention, the resins of the aforementioned Scholz et al. patents are modified somewhat by the use of a polyol containing a stable dispersion of hydrophobic polymeric particles which serve to reduce foaming during cure. Curable resins incorporating such polymeric particles are disclosed in U.S. patent application Ser. No. 07/376,421, filed on the same date as the present application, filed in the names of Charles C. Polta and Matthew T. Scholz under Express Mailing Certificate No. B75869802, and entitled "Curable Resins with Reduced Foaming Characteristics and Articles Incorporating Same"; such patent application is incorporated herein by reference.

As disclosed in the aforementioned concurrently filed patent application, preferable polyurethane prepolymer resins are prepared by reacting a polyisocyanate with a polyol having polymeric particles dispersed therein which serve to reduce foaming during cure and provide other benefits. Preferably, such polymeric particles are made from hydrophobic vinyl monomers. However, any monomers may be employed which will form polymeric particles that act to significantly reduce foaming. Polymeric particles which have been found suitable for this purpose include polyacrylonitrile, a copolymer of acrylonitrile and styrene, and polyurea (formed, for example, from toluene diisocyanate and ethylenediamine). Polymeric particles made from epoxy based resins or combinations of any of the foregoing would also be suitable.

Several polyols are commercially available which already have such polymeric particles dispersed therein, and are thus suitable for practicing the invention. For example, Niax E-562 polyol (available from Union Carbide Corporation, Wheeling, W.V.) which contains polymeric particles made of a copolymer of acrylonitrile and styrene (in a 50/50 weight % ratio); Niax E-701 polyol (also available from Union Carbide Corporation) which contains polymeric particles made of polyacrylonitrile; and Multranol 9151 polyol (available from Mobay Chemical Corporation, Pittsburgh, Pa.) which contains polymeric particles made of a polyurea; have been found to be useful in practicing the present invention. The presently most preferred polyols having polymeric particles dispersed therein are the aforementioned Niax E-562 and Niax E-701 polyols, which are referred to by Union Carbide Corporation as "Niax Performance Polyether Polymer Polyols."

Preferably, the polyols contain polymeric particles having an average diameter of less than about 20 microns. Preferably, the average diameter of the polymeric particles is greater than about 0.01 micron. At present, the polymeric particles more preferably have an average diameter of from about 0.01 microns to about 10 microns, and most preferably from about 0.3 microns to about 5 microns. However, there apparently is no minimum average diameter of particle needed to achieve the benefits of the invention, and it is believed that smaller particle sizes work best. Although polymeric particle sizes greater than the foregoing may be employed, it is believed that some of the benefits of the polymeric particles may be sacrificed if the particle sizes are too high.

Moreover, in the commercially available polyols mentioned herein, the polymeric particles comprise from about 20% to about 38% by weight of the polyol. It is believed that polyols containing 10% to 45% by weight function adequately. When incorporating such polymeric particle containing polyols into the curable resins of the present invention, the polymeric particles preferably comprise from about 0.5% to about 10% by weight of the resin, more preferably from about 1% to about 6% by weight of the resin, and most preferably from about 2% to about by weight of the resin.

Foaming of the resin-impregnated material (upon immersion in water) which would reduce the porosity of the cured material and its overall strength can also be minimized by using a foam suppressor such as DB-100 silicone fluid (Dow Corning) (now believed to be available under a new name, namely, Dow Corning Antifoam 1400), silicone Antifoam A (Dow Corning, Midland, Mich.), or silicone surfactant L550 or L5303 (available from Union Carbide) to the resin. It is presently preferred to use the Dow Corning DB-100 silicone fluid (or Dow Corning Antifoam 1400) at a concentration of about 0.1% to about by weight of the resin.

The curable resins used in the present invention are polymerizable to a thermoset state. Preferably, the curable resins have viscosities within the range of from about 10,000 centipoise to about 300,000 centipoise when measured on a Brookfield RVT Viscometer using spindle #6, more preferably within the range of from about 10,000 centipoise to about 100,000 centipoise, and most preferably within the range of from about 10,000 centipoise to about 80,000 centipoise. The resin is preferably nontoxic in the sense that it does not give off significant amounts of toxic vapors during curing which may be harmful to either the patient or the person applying the orthopedic casting material, and also in the sense that it does not cause skin irritation either by chemical irritation or by the generation of excessive heat during cure. Furthermore, the resin must be sufficiently reactive with the curing agent (e.g., water, where water curable resins are concerned) to ensure rapid hardening of the orthopedic casting material once it has been applied, but not so reactive that it does not allow for sufficient working time to apply and shape the orthopedic cast or splint. Initially, the orthopedic casting material must be pliable and conformable and should adhere to itself. Then in a short time following the completion of application, it should become rigid, or at least semi-rigid, and strong enough to support the loads and stresses to which the cast or splint is subjected by the activities of the wearer. Thus, the orthopedic casting material must undergo a change of state from a flexible condition to a relatively rigid condition in a matter of minutes.

As mentioned, the presently preferred resins are those which are cured with water. A number of classes of water curable resins are known in the art and are suitable for purposes of the present invention, including polyurethanes, cyanoacrylates esters (preferably used in conjunction with a suitable filler material such as polycyanoacrylate), and, when combined with moisture sensitive catalysts, epoxy resins and prepolymers terminated at their ends with trialkoxy-silane or trihalosilane groups. With regard to epoxy resins, it is noted that U.S. Pat. No. 3,932,526 discloses 1,1-bis(perfluoromethylsulfonyl)-2-aryl ethylenes which cause epoxy resins containing traces of moisture to become polymerized.

Resin systems other than those which are water curable may be used, although the use of water to activate the hardening of the orthopedic casting materials is presently the most convenient, safe, and familiar to orthopedic surgeons and medical casting personnel. For example, resin systems employing difunctional acrylates or methacrylates, such as the bis-methacrylate ester disclosed in U.S. Pat. No. 3,908,644, which ester is derived from the condensation of glycidyl methacrylate and bisphenol A (4,4'-isopropylidenediphenol), may be used. Such a resin system is hardened upon wetting with solutions of a tertiary amine and an organic peroxide. Further, U.S. Pat. No 3,630,194 discloses an orthopedic tape impregnated with acrylamide monomers whose polymerization is initiated by dipping the orthopedic tape in an aqueous solution of oxidizing and reducing agents (known in the art as a redox initiator system).

The presently preferred resins used in conjunction with the present invention cure to form a relatively rigid structure or cast. However, in some instances, such as sports medicine applications, a somewhat flexible resin may be desired to form a semi-rigid and resilient support upon curing. Examples of suitable flexible resins which may be used for this purpose are disclosed in commonly assigned copending patent application Ser. No. 903,281, filed Sep. 3, 1986, no U.S. Pat. No. 4,968,542, and commonly assigned copending patent application Ser. No. 083,685 filed Aug. 7, 1987, now U.S. Pat. No. 4,893,617, which applications are incorporated herein by reference.

As mentioned, the presently most preferable resins used in the present invention are water curable, isocyanate functional, polyurethane prepolymer resins. These resins are prepared by reacting a polyisocyanate with a polyol, as disclosed, for example, in U.S. Pat. No. 4,502,479. However, other urethane resins formed by the reaction of a polyisocyanate and a polyol, such as disclosed in U.S. Pat. No. 4,131,114, may also be used.

Thus, as used herein, a "water curable, isocyanate functional, polyurethane prepolymer" means a prepolymer derived from a polyisocyanate, preferably aromatic, and a polyol (or reactive hydrogen compound or oligomer). The polyurethane prepolymer has sufficient isocyanate functionality to cure (in the presence of a suitable catalyst) upon exposure to water, either in the form of moisture vapor, or more preferably, in the form of liquid water.

In forming the preferred water curable, isocyanate functional, polyurethane prepolymers of the present invention, it is preferred to use an isocyanate which has a relatively low volatility, such as diphenylmethane diisocyanate (MDI), rather than a more volatile material such as toluene diisocyanate (TDI). Presently preferred isocyanates include 4,4'-diphenylmethane diisocyanate, 2,4'-diphenylmethane diisocyanate, and mixtures of these isomers together with possible small quantities of 2,2'-diphenylmethane diisocyanate (typical of commercially available diphenylmethane diisocyanate). However, isocyanates such as aromatic polyisocyanates and their mixtures which are derived from phosgenation of the condensation product of aniline and formaldehyde may also be used.

Polyols which may be used to form the polyurethane prepolymers of the present invention include polypropylene ether glycols (available from Union Carbide, Danbury, Conn. as Niax TM PPG and from BASF Wyandotte Corp., Parsippany, N.J. as Pluracol TM P), polybutylene ether glycols (available from Dow Chemical, Midland, Mich. as XAS 10961.00 experimental polyol), polytetramethylene ether glycols (available from Quaker Chemical Company, Conshohocken, Pa. as Polymeg TM), polycaprolactone diols (available from Union Carbide as the Niax TM PCP series of polyols), and polyester polyols (hydroxyl terminated polyesters obtained from the esterification of dicarboxylic acids and diols such as the Lexorezp TM polyols available from Inolex Corp., Chemical Division, Philadelphia, Pa.). As will be appreciated by those skilled in the art, the rigidity of the cured resin can be reduced by increasing the molecular weight of the polyols, or conversely, the rigidity can be increased by using lower molecular weight polyols.

It will be understood that, as used herein, the term "polyol" also includes virtually any functional compound having active hydrogen in accordance with the well-known Zerevitinov test, as described, for example, in Chemistry of Organic Compounds by Carl R. Noller, Chapter 6, pp. 121–122 (1957). Thus, for example, thiols and polyamines could also be used as "polyols" in the present invention, and the term "polyols" will be considered to include such other active hydrogen compounds.

One example of a presently preferred resin which may be used in the present invention involves the reaction of an isocyanate known as Isonate TM 2143L (a mixture containing about 73% MDI) which is available from the Dow Chemical Company, Midland, Mich. with a mixture of polypropylene oxide polyols which are available from Union Carbide and are known as Niax TM PPG 2025 and Niax TM LG-650. To prolong the shelf life of the resin material, it is also preferable to include from about 0.01% to about 1% by weight of benzoyl chloride or other suitable stabilizer.

The reactivity of the curable resin, once it is exposed to the water or other curing agent, can be controlled by the use of a proper catalyst. The reactivity must not be so great that: (1) a hard film quickly forms on the resin surface preventing further penetration of the water into the bulk of the resin, or (2) the cast or splint becomes rigid before the application and shaping thereof has been completed. To produce suitable orthopedic casts and splints in accordance with the present invention, a set time of from about 2 to about 18 minutes following activation of the curable resin is preferred, with a more preferable set time being from about 2.5 to about 10 minutes, and a most preferable set time being from about 3 to about 5 minutes. Thus, the curable resins of the present invention also preferably contain a catalyst to control the set time and cure time of the resin.

Suitable catalysts for moisture curing polyurethane prepolymer resin systems are well known. For example, tertiary amine catalysts such as 4-[2-[1-methyl-2-(4-morpholinyl)ethoxy]ethyl]morpholine (MEMPE) described in commonly assigned, U.S. Pat. No. 4,705,840 (Buckanin), in amounts ranging from about 0.5% to about 5% by weight of the resin system, may be used for this purpose. The MEMPE catalyst disclosed in U.S. Pat. No. 4,705,840, which patent is incorporated herein by reference, is the presently preferred catalyst system for use in connection with the present invention.

As mentioned, it is also preferred to make the curable resin of the present invention less tacky in accordance with the invention described in commonly assigned U.S. Pat. No. 4,667,661 (Scholz et al.) and U.S. Pat. No. 4,774,937 (Scholz et al.). Reduced tackiness may be achieved by a number of means as described in U.S. Pat. No. 4,667,661 and U.S. Pat. No. 4,774,937. One technique for achieving such tack reduction is to lightly coat the surfaces of the resin-coated scrim with a mixture of a polydimethylsiloxane, having a viscosity of at least about 100 centistokes, and polyethylene oxide long chain aliphatic hydrocarbon waxes. Alternatively, a small amount of a polyethylene oxide-polypropylene oxide block copolymer (such as Pluronic F-108 available from BASF Wyandotte) may be added to the resin during prepolymer preparation, after which the polydimethylsiloxane may be applied onto the surface of the orthopedic article as before. The polydimethylsiloxane reduces resin tackiness prior to contact with water. The hydrophilic polyethylene oxide materials provide additional tack reduction upon contact with water.

The preparation of the orthopedic casting materials of the present invention generally involves the simple coating of the curable resin onto the fabric scrim. Generally, the scrim should be resin loaded to the point where the resin represents from about 35% to about 80% by weight of the total weight of the resin-coated scrim. In the case of a fiberglass scrim, the resin preferably represents from about 35% to about 60% by weight of the total weight of the resin-coated scrim, and preferably from about 38% to about 45% by weight. Manual or mechanical manipulation of the resin (such as by a nip roller or wiper blade) into the scrim is usually not necessary. However, some manipulation of the resin into the fabric may sometimes be desirable. Care should be given not to stretch the fabric scrim during resin coating, however, so as to preserve the stretchability of the material for its later application around the desired body part.

Orthopedic casting materials prepared in accordance with the present invention are applied to humans or other animals in the same fashion as other known orthopedic casting materials. First, the body member or part to be immobilized is preferably covered with a conventional cast pad or stockinet to protect the body part. Next, the curable resin is activated, for example, by dipping the orthopedic casting material in water in the case of a water curable resin. Excess water may then be squeezed out of the orthopedic casting material, and the material is wrapped or otherwise positioned around the body part so as to properly conform thereto. Preferably, the material is then molded and smoothed to form the best fit possible and to properly secure the body part in the desired position. Although often not necessary, if desired, the orthopedic casting material may be held in place during cure by wrapping an elastic bandage or other securing means around the curing orthopedic casting material. When curing is complete, the body part is properly immobilized within the orthopedic cast or splint which is formed.

Reference will now be made to the figures, wherein like parts are designated with like numerals throughout, and wherein several methods of manufacturing the resin-coated materials of the present invention will now be explained.

Figure 2:
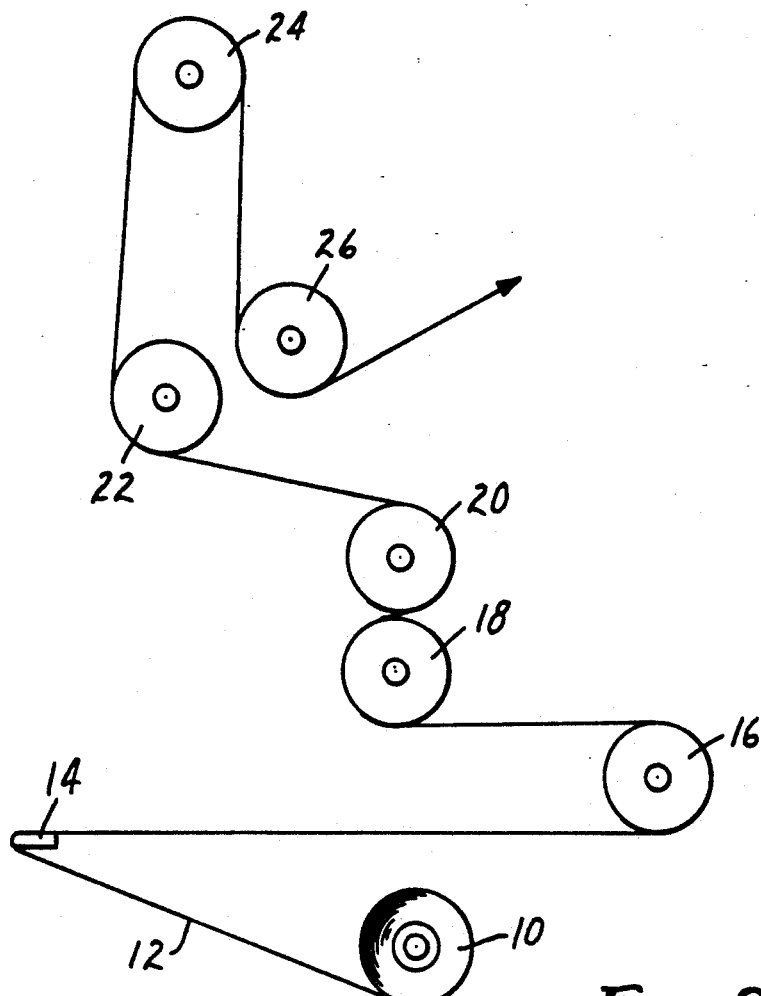
FIG. 2 is a schematic illustration of one method for forming projections along a scrim in accordance with the present invention.

Referring now to FIG. 2, one method within the scope of the present invention for forming projections along a scrim is illustrated. First, a supply wheel containing a jumbo supply roll 10 of knitted fiberglass fabric tape is provided, and the fiberglass scrim 12 is unwound from the supply roll 10 and into the processing line. The tension on the supply roll 10 is controlled by a conventional clutch (not shown) for example, a Sperry Magneclutch® 5MC90B, available from Sperry, St. Paul, Minn. The clutch setting is preferably set at either 0.5 or 1.0 pounds (0.23 or 0.46 kg), depending upon the level of abrading desired. The higher the tension, the greater the level of abrading obtained. In this regard, it has been found that settings much over 1 pound cause a heat-set fiberglass scrim to break.

The fiberglass scrim 12 is then passed over a carbide blade 14 which, in one preferred embodiment, is 1 inch (2.54 cm) wide (in the horizontal direction of FIG. 2) and ⅛ inch (0.32 cm) thick (in the vertical direction of FIG. 2) with the scrim bending around the blade at an angle of about 30 degrees. As the scrim 12 passes along carbide blade 14, projections are formed along scrim 12 in accordance with the teachings of the present invention. From blade 14, the fabric scrim passes around an idler roller 16 which directs the scrim to another idler roller 18. A motor driven, rubber coated roller 20 provides the driving force for pulling the scrim through the processing line, and motor driven roller 20 receives the fabric scrim from idler 18 and pulls the scrim at a web speed of about 80 feet per minute (24.4 meters/minute).

From motor driven roller 20, scrim 12 passes to a series of adjustable rollers 22, 24, and 26, which serve to steer the scrim web 12 and align it with a resin coating head (not shown) further downstream. There, scrim 12 is coated with a curable resin within the scope of the present invention.

Figure 3:
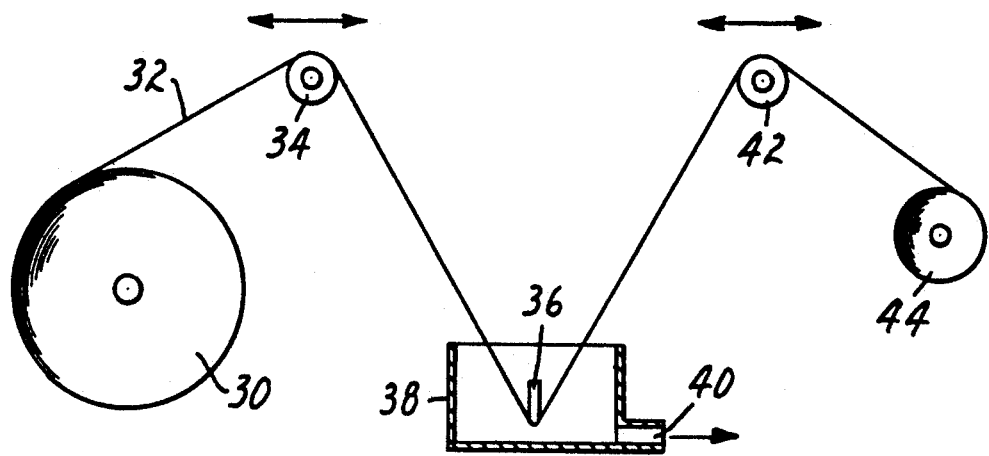
FIG. 3 is a schematic illustration of yet another method for forming projections along a scrim in accordance with the present invention.

Referring now to FIG. 3, another method for forming projections along a scrim within the scope of the present invention is illustrated. In this embodiment, a jumbo supply roll 30 of fiberglass fabric is unrolled as scrim 32, which passes over idler roller 34. The tension of scrim 32 may be controlled by a magnetic particle clutch, such as that discussed in the embodiment of FIG. 2 above. Scrim 12 passes downwardly over a carbide blade 36 which, in one embodiment, is 0.75 inches (1.9 cm) wide (in the vertical direction of FIG. 3) and ⅛ inch (0.32 cm) thick (in the horizontal direction of FIG. 3), and is adjustable so that the angle at which the scrim 12 passes around blade 36 may be adjusted from about 30 degrees to about 60 degrees. When passing scrim 32 over blade 36, projections within the scope of the present invention are formed along scrim 32.

Because fibers may be released when abrading scrim 32 with blade 36, in this embodiment, blade 36 is mounted within a containment box 38 having a bottom outlet 40 which is connected to a vacuum source (not shown) to allow the released fibers or any other debris created by the abrading process to be drawn away. Removing the released fibers in this fashion serves to minimize operator contact with airborne fibers which might pose a health hazard. Scrim 32 is then drawn up and over an idler roller 42 by a motor driven take-up roll 44 where the abraded scrim is collected.

Figure 4:
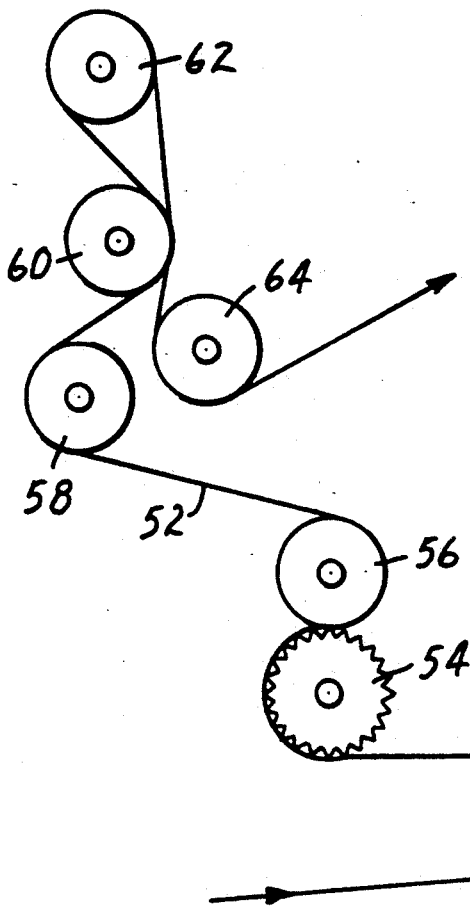
FIG. 4 is a schematic illustration of the presently most preferred method for forming projections along a scrim in accordance with the present invention.

Referring now to FIG. 4, the presently most preferred method for forming projections along a scrim within the scope of the present invention is schematically illustrated. In this presently most preferred embodiment, supply roll (not shown) of knitted fiberglass material is unwound as fabric scrim 52 in preparation for abrasion.

Scrim 52 passes first around idler roller 50, then passes around knurled roller 54 and between knurled roller 54 and a smooth, motor driven, rubber coated roller 56. Knurled roller 54 is an idler roller and is preferably configured so as to have a straight knurl with sharp teeth. Means for adjusting the force or pressure (not shown) between knurled roller 54 and motor driven roller 56 are also provided. By adjusting the amount of force between knurled roller 54 and motor driven roller 56, the amount of abrasion, and hence the number of projections formed, can be controlled. After passing through the space between knurled roller 54 and motor driven roller 56, projections are formed along one surface of scrim 52 in accordance with the present invention.

The "abrasion" achieved by passing scrim 52 between rollers 54 and 56 is actually a process which results in the physical fracture of some of the fibers in scrim 52. In this regard, as scrim 52 passes between the knurled roller 54 and the smooth, motor driven roller 56, the action of rollers 54 and 56 on the scrim 52 therebetween bends the glass fibers of scrim 52 to a point past a critical bending angle, thereby resulting in a physical fracture of some of the fiber. The proper force or pressure employed between rollers 54 and 56 depends upon such factors as the size and number of fibers in the scrim, and the sizing condition of the scrim. (Although it is presently preferred to desize the scrim before forming projections thereon in accordance with the present invention, if desired, the present invention may also be used to provide projections along scrims which have not been desized.)

Figure 5:
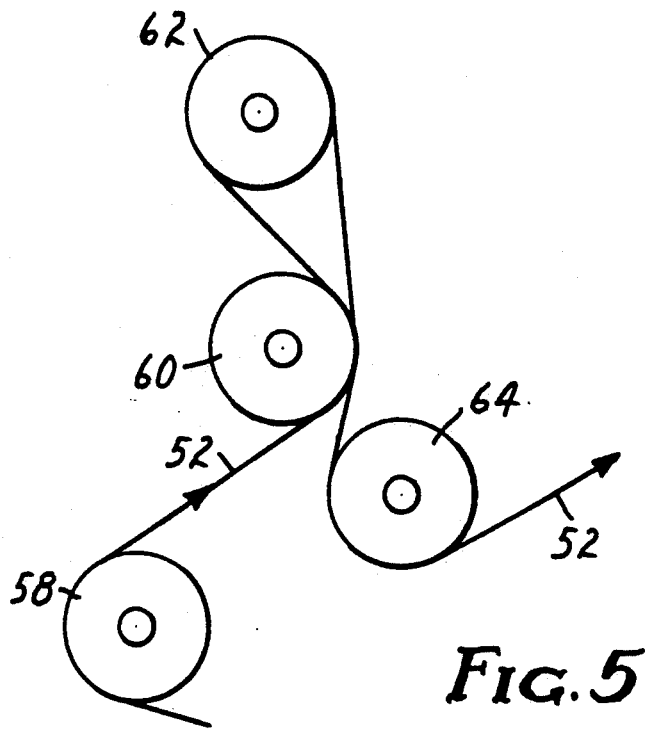
FIG. 5 is an enlarged view of a portion of the schematic illustration of FIG. 4 illustrating one method for passing the abraded scrim over itself in order to encourage the projections formed thereon to stand up and away from the surface of the scrim material.

Referring now to both FIGS. 4 and 5, from motor driven roller 56, scrim 52 passes to idler roller 58 which directs the scrim to an adjustable rubbing roller 60. The scrim 52 then passes up and around idler roller 62, and then down to idler roller 64 where it is drawn away for coating with an appropriate resin.

As can be seen in FIGS. 4 and 5, the abraded surface of scrim 52 which is directly adjacent adjustable roller 60 passes along and rubs against the abraded surface of scrim 52 extending between idler rollers 62 and 64 in a countercurrent fashion. By rubbing the abraded surfaces of the scrim together in this fashion, the projections are encouraged to stand up and away from the fabric scrim. Means (not shown) may also be provided for adjusting the position of rubbing roller 60 so as to increase or decrease the amount of rubbing pressure between the countercurrent scrim surfaces.

As mentioned, the resin-coated materials of the present invention exhibit surprising resistance to delamination (delamination strength). Additionally, because the present invention provides a means for achieving superior lamination, lighter weight scrims and scrims having yarns with larger and fewer filaments can be used in the scrims of the present invention than are used in the scrims of the prior art. Furthermore, because the projections of the present invention increase lamination, lesser amounts of resin can be employed and scrims may be employed in the present invention which would not have adequate resin holding capacity at the higher conventional resin loading levels necessary in the prior art. As a result of the foregoing benefits, many scrims which were unsuitable for use in the prior art may indeed be employed successfully in the present invention, often at a significantly reduced cost.

Summarized below are tests which were used to determine the "delamination strength" as well as the "ring strength" (measured in 3 different ways: "dry strength", "wet strength", and "warm wet strength"). Hence, whenever the terms "delamination strength" or "ring strength" (including the terms "dry strength", "wet strength", and "warm wet strength") are used herein, it will be understood that these terms refer to the delamination test and strength tests set forth hereinbelow, and that the values given for "delamination strength" and "ring strength" were determined in accordance with the following tests.

DELAMINATION TEST

This test measured the force necessary to delaminate a cured cylindrical ring of a resin-coated material within the scope of the present invention.

Each cylindrical ring comprised 6 layers of the resin-coated material having an inner diameter of 2 inches (5.08 cm). The width of the ring formed was the same as the width of the resin-coated material employed, namely, 3 inches (7.62 cm). (The final calculation of the delamination strength is given in terms of newtons per centimeter of tape width.)

Each cylindrical ring was formed by taking a roll of the resin-coated material from its storage pouch and immersing the roll completely in deionized water having a temperature of about 80° F. (27° C.) for about 30 seconds. The roll of resin-coated material was then removed from the water and the material was wrapped around a 2 inch (5.08 cm) mandrel covered with a thin stockinet (such as 3M Synthetic Stockinet MS02) to form 6 complete uniform layers using a controlled wrapping tension of about 45 grams per centimeter width of the material. A free tail of about 6 inches (15.24 cm) was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

This was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample at a speed of about 127 cm/min. The average force required to delaminate the wrapped layers over the first 33 centimeters of the cylinder was then recorded in terms of force per unit width of sample (newtons/cm). For each material, at least 5 samples were tested, and the average delamination force was then calculated and reported as the "delamination strength."

In the practice of the present invention, delamination strengths of up to 14 newtons/cm have been observed.

If better delamination strength is observed when performing this delamination strength test for the resin-coated materials having projections formed thereon in accordance with the disclosure herein over resin-coated materials made from the same scrim material and same resin only without projections formed on the scrim, the projections on the former resin-coated materials are considered to "enhance lamination" and are thus considered to be within the scope of the present invention.

RING STRENGTH TESTS

In these tests, the "dry strength", "wet strength", and "warm wet strength", of certain cured cylindrical ring samples of the resin-coated materials of the present invention were determined. For each of these tests, cured cylindrical ring samples were formed as described hereinabove with respect to the delamination test so as to form 6-layered cylinders around a 2-inch (5.08 cm) mandrel, only all excess material was trimmed off to form these cylindrical rings, leaving no tails.

At a point 30 minutes following the initial immersion in water, each cylinder was removed from its respective mandrel and allowed to cure for 48-60 hours in a controlled atmosphere of 75° F.±3° F. (34° C.±2° C.) and 55%±5% relative humidity. Each cylinder was then placed in a fixture in a commercial testing instrument, e.g., an Instron instrument, and compression loads were applied to the cylindrical ring sample along its exterior and parallel to its axis. The cylindrical ring was placed lengthwise between the two bottom bars of the fixture (the bars being 1.9 centimeters wide, 1.3 centimeters in height, and 15.2 centimeters long), with the bars spaced about 4 centimeters apart. The inside edges of the bars were machined to form a curved surface having a ⅛ inch (0.31 cm) radius. A third bar (0.63 cm wide, 2.5 cm high, and 15.2 cm long) was then centered over the top of the cylinder, also parallel to its axis. The bottom or contacting edge of the third bar was machined to form a curved surface having a ⅛ inch (0.31 cm) radius. The third bar was brought down to bear against and crush the cylinder at a speed of about 5 cm/min. The maximum or peak force which was applied while crushing the cylinder was then recorded as the ring strength, which in this particular instance is the "dry strength" (expressed in terms of force per unit length of the cylinder, i.e., newtons/cm). For each material, at least 5 samples were tested, and the average peak force applied was then calculated and reported as the "dry strength."

To measure the "wet strength", the same procedure was followed as for the "dry strength", except that after curing for 48-60 hours, the cylinder was then immersed in water at about 113° F. (45° C.) for about 30 minutes, and then allowed to dry under ambient conditions for about 15 minutes. The cylinder was then placed in the instrument and crushed as described hereinabove in order to determine the "wet strength" thereof.

To determine the "warm wet strength" of the cylinder, the procedure was followed exactly as set forth for the "wet strength" measurement above, with the exception that the cylinder was placed in the fixture and crushed immediately after removal from the 113° F. (45° C.) water bath and was not allowed to dry at all.

The following examples are given for purposes of illustration only, and should not be considered comprehensive or restrictive.

EXAMPLE 1

In this example, the number of projections on different samples of fabric were determined and compared. Ten groups of samples, with 3 experimental fabric sections in each sample group, were observed and compared (with the exception of sample group 1, which comprised a single fabric section in the experiment). Sample groups 1, 5, and 9 represent unabraded or otherwise untreated fabrics which are not within the scope of the present invention (and thus are comparative sample groups), while sample groups 2-4, 6-8, and 10 represent abraded fabrics having populations of projections within the scope of the present invention.

Sample groups 1-4 involve the use of a heat-set, knitted fiberglass fabric knit into the Scotchcast ® 2 scrim pattern using ECG 75 1/0 0.7Z fiberglass yarn obtained from Owens Corning Fiberglass. Sample groups 5-8 involve the use of a heat-set, knitted fiberglass fabric knit into the Scotchcast ® 2 scrim pattern using ECDE 75 1/0 1.0Z fiberglass yarn obtained from either PPG Industries or Owens Corning Fiberglass. (The number of twists per unit length of yarn varies in the 1.0Z and 0.7Z scrims used herein. However, the difference in the number of twists has not been observed to have any significant effect on the results achieved in the present invention.) Sample groups 9-10 involve the use of a heat-set, knitted fiberglass fabric knit into the same scrim pattern and using the same fiberglass yarn (namely, ECDE 75 1/0 1.0Z fiberglass yarn obtained from either PPG Industries or Owens Corning Fiberglass) as used in 3M's Scotchflex ® Extrafast product. The Scotchflex ® scrim is a 2 bar, 18 gauge (9 needles per inch) Raschel warp knit construction for which every other guide and needle are removed; the front bar executes an open chain stitch and the back bar lays in; the pattern notation is 2-0, 0-2 and 0-0, 8-8 for the front and back bars, respectively; the runner lengths are 128 inches and 117 inches for the front and back bars; the fabric has approximately 7 wales per inch and 17 courses per inch.

None of the fiberglass fabrics of sample groups 1, 5, or 9, was abraded, and represent prior art fiberglass fabrics without the lamination benefits of the present invention. Each of the fiberglass fabrics of sample groups 2-4, 6-8, and 10 were abraded in accordance with the presently most preferred method of manufacture which is schematically represented in FIG. 4. In this regard, the force between the drive roller and the knurled roller of FIG. 4 was set at 67 lbs. (300 newtons) for each of sample groups 2, 6, and 10; at 100 lbs. (450 newtons) for each of sample groups 3 and 7; and at 134 lbs. (600 newtons) for each of sample groups 4 and 8. (It should be noted that the much lighter weight fiberglass scrim of sample groups 9 and 10 could not endure forces of 100 lbs. (450 newtons) or higher without being shredded and substantially destroyed so as to preclude any further observation or testing.)

After preparation of the fiberglass fabric sample groups 1-10, a polyurethane prepolymer resin having the following formulation was coated onto each of the fiberglass fabrics at a coating weight of about 40% resin for sample groups 1-4, about 42.5% resin for sample groups 5-8, and about 44% resin for sample groups 9-10:

| Ingredient | Weight % | Equivalent Weight |
|---|---|---|
| Isonate 2143L (Available from Dow Chemical, Midland, MI) | 56.64 | 144 |
| Benzoyl Chloride | 0.05 | 141 |
| DB-100 Silicone Antifoam (Available from Dow Corning, Midland, MI) | 0.18 | Not Applicable (N/A) |
| Butylated Hydroxytoluene | 0.48 | N/A |
| MEMPE Catalyst (From U.S. Pat. No. 4,705,840) | 1.32 | 129 |
| PPG-424 Polyol (Available from Union Carbide, Danbury, CT) | 11.8 | 212 |
| PPG-725 Polyol (Available from Union Carbide) | 25.53 | 375 |
| Pluronic F-108 (Available from BASF Wyandotte Corp., Parsippany, NJ) | 4.0 | 7,250 |

The resin was then removed from each of the fiberglass fabrics of sample groups 1-10. To achieve this, packaged rolls of the resin-coated tapes of sample groups 1-10 were removed from their respective packages in a dry environment (less than 4% relative humidity), and three 40 cm lengths of the resin-coated tape were cut from each roll, taking care not to touch the surface of the tape where measurements would later be taken. Each of the resin-coated tape samples from groups 1-10 was folded upon itself 4 times so as to form a fan-folded configuration, and the tape was gently placed in a foil pouch and sealed. Each tape was hen transferred to a ventilated hood area where the sample was removed from its pouch, placed in a 12 centimeter diameter buchner funnel on a piece of Whatman number 1 filter paper. Six liters of a 50/50 solution (by weight) of tetrahydrofuran/methanol was slowly passed over the fan-folded sample and allowed to pass through the filter in order to dissolve off most of the resin from the fiberglass scrim of the sample. Extreme care was taken during this procedure so as not to disturb the surfaces of the tape and to ensure that the rinsed taped was substantially free of resin (less than 5% by weight resin). Each tape sample was then dried in an oven at a temperature of 120° F. (49° C.) for a period of about 15 minutes.

Although major differences were not observed in the surface properties and numbers of projections between the uncoated fiberglass scrims and the fiberglass scrims after resin removal, these sample groups 1-10 illustrate the numbers of projections observed after resin removal from the fiberglass scrims.

The fiberglass fabric sections observed in each of sample groups 1-8 had a width of 8 centimeters, and a length of 5 centimeters. To achieve this, three nonconsecutive 5 centimeter lengths were chosen at random and carefully marked off along the fiberglass tape (which was already 8 centimeters wide) of each of sample groups 2-8, with about 10 centimeter lengths of unobserved material being left between each of the three observed sections and with about 5 centimeter lengths being left between the ends of the tape sample and the observed sections. (Only one such fabric section was marked off and observed for sample group 1.) Thus, to minimize handling of the material, the three fabric sections for each sample group were merely marked off along the same tape rather than actually cutting out the individual fabric sections. The same procedure was used for sample groups 9 and 10 except that the width of the fiberglass tape (and hence of each fabric section) was 8.5 centimeters.

Each fabric section was carefully draped over a piece of cardboard (having a thickness of 1 mm) first in the widthwise direction and then in the lengthwise direction, while avoiding contact with the surface to be observed. Each time, the fabric section was placed so as to extend over the edge of the cardboard with a minimum amount of tension being applied to the sides of the fabric so as to flatten it out over the corresponding sides of the cardboard. By holding the fiberglass fabric samples over the edge of the cardboard, the filament bundles were more readily observable under a microscope (using a lens of about 10 to 20 power), allowing the numbers of filaments per bundle to be counted, and allowing the numbers of projections (those filament bundles having 8 or more filaments) to be counted along the edge of the cardboard.

The number of filament bundles qualifying as "projections" (those having 8 or more filaments in the bundle) were counted both in the widthwise and lengthwise directions; these values are reported in Table I below. The number of projections per square centimeter for each of the samples was then calculated, and the average number of projections/cm$^3$ for the fabric sections observed in sample groups 1-10 was calculated; these figures also appear in Table I below.

The fiberglass scrim of sample groups 1-4 had a basis weight of 0.031 grams per square centimeter; the fiberglass scrim of sample groups 5-8 had a basis weight of 0.031 grams per square centimeter; and the fiberglass scrim of sample groups 9-10 had a basis weight of 0.0118 grams per square centimeter. (These basis weights were determined using fabric samples from which the resin had been removed as previously described herein, and after placing the fabric samples in a 1200° F. (649° C.) oven for about 3 minutes so as to burn off substantially any resin residue remaining on the fabric samples.) As will be noted, the fiberglass scrim involved in sample groups 9-10 is a very lightweight, open fabric; this fiberglass fabric has only an average of about 10 yarns per centimeter along the lengthwise direction of the fabric. Using the basis weight of each of the fabrics and the average number of projections per square centimeter, the average number of projections per gram of fiberglass scrim in each sample group was calculated. Again, this information is reported in Table I below.

TABLE I

| Sample Group | Fiberglass Yarn | Force Between Rollers (newtons) | Projections Along 8/8.5 cm Width | Projections Along 5 cm Length | Projections/ cm$^2$ | Average Projections/ cm$^2$ | Average Projections/ gram fiberglass |
|---|---|---|---|---|---|---|---|
| 1 | ECG | 0 | 0 | 0 | 0 | 0 | 0 |
| 2 | ECG | 300<br>300<br>300 | 32<br>26<br>22 | 28<br>12<br>15 | 22.40<br>7.80<br>8.25 | 12.8 | 418 |
| 3 | ECG | 450<br>450<br>450 | 36<br>46<br>32 | 21<br>15<br>16 | 18.90<br>17.25<br>12.80 | 16.3 | 532 |
| 4 | ECG | 600<br>600<br>600 | 56<br>60<br>58 | 17<br>20<br>13 | 23.80<br>30.00<br>18.85 | 24.2 | 789 |
| 5 | ECDE | 0<br>0<br>0 | 2<br>3<br>5 | 1<br>0<br>1 | 0.05<br>0.00<br>0.13 | 0.06 | 1.90 |
| 6 | ECDE | 300<br>300<br>300 | 27<br>24<br>31 | 7<br>5<br>12 | 4.73<br>3.00<br>9.30 | 5.7 | 185 |
| 7 | ECDE | 450<br>450<br>450 | 59<br>34<br>33 | 15<br>10<br>8 | 22.13<br>8.50<br>6.60 | 12.4 | 404 |
| | | 600 | 41 | 34 | 34.85 | | |

TABLE I-continued

| Sample Group | Fiberglass Yarn | Force Between Rollers (newtons) | Projections Along 8/8.5 cm Width | Projections Along 5 cm Length | Projections/ cm² | Average Projections/ cm² | Average Projections/ gram fiberglass |
|---|---|---|---|---|---|---|---|
| 8 | ECDE | 600<br>600 | 27<br>51 | 10<br>27 | 6.75<br>34.43 | 25.3 | 826 |
| 9 | ECDE | 0<br>0<br>0 | 1<br>2<br>4 | 1<br>3<br>5 | 0.02<br>0.14<br>0.47 | 0.2 | 17.9 |
| 10 | ECDE | 300<br>300<br>300 | 16<br>21<br>22 | 8<br>16<br>17 | 3.01<br>7.91<br>8.80 | 6.6 | 557 |

As seen in Table I above, the numbers of projections in each of comparative sample groups 1, 5, and 9 were either very small or insignificant. The numbers of projections calculated for each of sample groups 2–4, 6–8, and 10 are among the projection populations which provide enhanced lamination properties in the practice of the present invention.

EXAMPLE 2

Example 2 is a comparative example which was conducted to investigate if any "projections" might appear on CaraGlas ™ fiberglass casting tape (having a basis weight of about 0.029 grams per square centimeter) sold by Carapace, Inc., Tulsa, Okla. Hence, it will be understood that this Example 2 is included for purposes of comparison only, and is not within the scope of the present invention.

Since uncoated samples of the fiberglass fabric scrim used in CaraGlas ™ casting tape were not available, the resin was removed from commercially available samples of CaraGlas ™ orthopedic casting tape in order to determine if any projections might be observed along the surface thereof.

To achieve this, a roll of CaraGlas ™ orthopedic casting tape was removed from its package in a dry environment (less than 4% relative humidity), and three 40 cm lengths of the resin-coated tape (Samples A, B, and C) were cut from the roll, taking care not to touch the surface of the tape where measurements would later be taken. Each of resin-coated tape Samples A, B, and C was folded upon itself 4 times so as to form a fan-folded configuration, and the tape was gently placed in a foil pouch and sealed. Each sample was then transferred to a ventilated hood area where the sample was removed from its pouch, placed in a 12 centimeter diameter buchner funnel on a piece of Whatman number 1 filter paper. Six liters of a 50/50 solution (by weight) of tetrahydrofuran/methanol was slowly passed over the fan-folded sample and allowed to pass through the filter in order to dissolve off most of the resin from the fiberglass scrim of the sample. Extreme care was taken during this procedure so as not to disturb the surfaces of the tape and to ensure that the rinsed tape was substantially free of resin (less than 5% by weight resin). Each tape sample then dried in an oven at a temperature of 120° F. (49° C.) for a period of about 15 minutes.

After such time, each Sample A, B, and C, was removed from the oven, and 5 centimeter lengths were marked off along each tape so as to provide fabric sections having a length of 5 centimeters and a width of 8 centimeters. Each fabric section of Samples A, B, and C was then draped over a piece of cardboard using the same procedure as outlined in Example 1 above, in order to calculate the number of projections along the fabric section extending from the edge of the cardboard in both the lengthwise and widthwise directions.

In Sample A, no bundles of filaments were found in either the lengthwise or or widthwise direction having or more filaments. Hence, no "projections" were found in this Sample A. Along the 5 centimeter length of Sample A, the following filament bundles were observed: 3 bundles having 3 filaments, 1 bundle having 4 filaments, 1 bundle having 5 filaments, and 1 bundle having 6 filaments. Along the 8 centimeter width of Sample A, the following filament bundles were observed: 4 bundles having 4 filaments were the only filament bundles seen.

In Sample B, 3 filament bundles having 4 filaments each were observed along the 5 centimeter length, while along the 8 centimeter width 1 filament bundle having 8 filaments (thus qualifying as a "projection"), 1 filament bundle having 6 filaments, and 5 filament bundles having 4 filaments each were observed. Hence, there was 1 sole fiber bundle observed on Sample B which would qualify as a "projection" under applicants' definition of the same.

In Sample C, no "projections" were observed. Along the 5 centimeter length of Sample C, the following filament bundles were observed: 1 filament bundle having filaments, 2 filament bundles having 5 filaments, and 2 filament bundles having 4 filaments. Along the 8 centimeter width of Sample C, the following filament bundles were observed: 1 filament bundle having 5 filaments, 2 filament bundles having 4 filaments, and 2 filament bundles having 3 filaments.

Hence, from the foregoing, it was observed that the CaraGlas ™ fiberglass tape tested had practically no filament bundles which would qualify as projections within the scope of the present invention. (Significantly less than one projection per gram of fiberglass was observed.)

EXAMPLE 3

In this example, projections within the scope of the present invention were formed along a scrim in accordance with the process schematically set forth in FIG. 2. In this example, three different rolls of knitted fiberglass scrim were knitted using ECDE 75 1/0 1.0Z fiberglass yarn available from Owens Corning Fiberglass Corp., Toledo, Ohio, and were knitted to form the Scotchcast ® 2 scrim pattern. Two of the rolls (Rolls 1 and 2) were passed through the process line of FIG. 2, and the third roll (Roll 3) served as a control. The tension for each of the supply Rolls 1 and 2 was controlled in the processing line by a Sperry Magneclutch ® 5MC90B available from Sperry, St Paul, Minn., and the clutch setting was set for 0.5 pounds (0.23 kg) in one of the runs (Roll 1) and 1.0 pounds (0.46 kg) in one of the runs (Roll 2). The entire 200 yard (183 meter) jumbo roll was processed for each of Rolls 1 and 2, passing it over the blade to abrade the surface of the scrim.

Each jumbo Roll 1 and 2 was then again processed through the processing line of FIG. 2 a second time, abrading the opposed surface of the fabric layer. After the second abrasion step, a polyurethane prepolymer resin having the following formulation was coated onto each of Rolls 1 and 2 at a coating weight of about 42.5% (23.9 grams/meter$^2$) of the total weight of the resin-coated material:

| Ingredient | Weight % | Equivalent Weight |
|---|---|---|
| Isonate 2143L (Available from Dow Chemical, Midland, MI) | 56.64 | 144 |
| Benzoyl Chloride | 0.05 | 141 |
| DB-100 Silicone Antifoam (Available from Dow Corning, Midland, MI) | 0.18 | N/A |
| Butylated Hydroxytoluene | 0.48 | N/A |
| MEMPE Catalyst (From U.S. Pat. No. 4,705,840) | 1.32 | 129 |
| PPG-424 Polyol (Available from Union Carbide, Danbury, CT) | 11.8 | 212 |
| PPG-725 Polyol (Available from Union Carbide) | 25.53 | 375 |
| Pluronic F-108 (Available from BASF Wyandotte Corp., Parsippany, NJ) | 4.0 | 7,250 |

Roll 3 was not passed through the processing line of FIG. 2, but was coated with the above-outlined resin in the same manner and amount to serve as a control. Each of the three jumbo Rolls 1, 2, and 3 was then converted into 4 yard (3.7 meter) rolls (Roll Groups 1, 2, and 3), which were individually sealed in foil pouches. Some of the rolls from each roll group were then tested in accordance with the ring delamination tests set forth herein. The results of the ring delamination test are shown below in Table II and represent the average of at least 5 repetitions of the ring delamination test.

TABLE II

| | Roll Group 1 | Roll Group 2 | Control Roll Group 3 |
|---|---|---|---|
| Ring delamination strength (newtons/cm) | 8.91 | 9.10 | 4.01 |

As seen in Table II above, the rolls of Roll Groups 1 and 2 which were abraded in accordance with the present invention exhibited much improved ring delamination strength over the rolls of the Control Roll Group 3 which were not abraded in accordance with the present invention.

Sample rolls were also taken from each of Roll Groups 1-3, dipped in water and applied around a 2 inch (5.08 cm) diameter mandrel to simulate the application of an orthopedic cast. After about 10 minutes, the simulated casts made from Roll Groups 1 and 2 could not be unwrapped, but the simulated casts made from the Control Roll Group 3 were unwrapped relatively easily from several inches to several feet.

EXAMPLE 4

In this example, projections within the scope of the present invention were formed using the presently most preferred method which is schematically represented in FIG. 4. For this example, fiberglass yarn was obtained from Owens Corning, Toledo, Ohio as ECDE-75 1/0 1.0Z and from PPG Industries as ECG-75 1/0 0.7Z. Each yarn was knit into a Scotchcast ® 2 scrim pattern.

Two jumbo rolls comprising 220 yards (201 m) of the ECDE yarn fiberglass casting tape and 2 jumbo rolls comprising 220 yards (201 m) of the ECG yarn fiberglass casting tape were formed, and the rolls were de-sized and heat-set by heating at about 800°-900° F. for about 9 hours in a batch convection oven. One jumbo roll of the ECDE fiberglass fabric was simply coated with a curable resin and was not abraded (Sample 1). Another jumbo roll of the ECDE fiberglass fabric was abraded using the process of FIG. 4 and then coated with a curable resin (Sample 2). Similarly, one jumbo roll of the ECG fiberglass fabric was simply coated without being abraded (Sample 3), while the other jumbo roll of the ECG fiberglass fabric was abraded in accordance with the process of FIG. 4, and then coated with the curable resin (Sample 4). In abrading Samples 2 and 4, a web speed of from about 80 to about 100 feet per minute (24.4-30.5 m/sec) was employed in carrying out the process of FIG. 4. The material was then converted to 4 yard rolls which were wrapped around a ¾" core and sealed in a moisture-proof pouch.

For each of Samples 1-4, the resin employed was that disclosed in Example 3 above. For each or Samples 1 and 2, a coating weight of 42.5% (23.9 g/m$^2$) was used, while a coating weight of 40% (21.5 g/m$^2$) was used for Samples 3 and 4. The knurled roller used in accordance with the procedure of FIG. 4 had a straight knurl and sharp teeth, with 12 teeth per inch, and the force between the knurled roller 54 and the motor driven roller 56 of FIG. 4 was set at about 750 newtons. Four yard (3.7 meter) rolls were taken from each jumbo roll and were stored and tested for delamination as outlined above for Example 3. The results are reported in Table III below, using the average value for 5 repetitions of the ring delamination test.

TABLE III

| | Sample 1 | Sample 2 | Sample 3 | Sample 4 |
|---|---|---|---|---|
| Ring delamination strength (newtons/cm) | 8.02 | 13.70 | 7.83 | 12.43 |

Again, as seen in Table III above, significantly improved lamination properties were achieved in Samples 2 and 4 which were abraded in accordance with the present invention over Samples 1 and 3 which were the respective unabraded control samples.

EXAMPLE 5

In this example, resin-coated Samples 5-14 were prepared in accordance with the procedure and parameters of Example 4 where the ECDE fiberglass yarn was employed in Samples 5-9 and the ECG fiberglass yarn was employed in Samples 10-14. Samples 6-9 and 11-14 were abraded as in Example 4. (Samples 5 and 10 were controls prepared in the same fashion as the Control Samples 1 and 3 of Example 4 and were not abraded using the process of FIG. 4 of the present invention.) The only exception to the Example 4 procedure was that the force between knurled roller 54 and motor driven roller 56 of FIG. 4 was varied somewhat in order to investigate the effect of force between the two rollers in Samples 6-9 and 11-14 of this Example 5. The coating weights for the two different types of fiberglass scrims (ECDE and ECG) was the same as set forth for those scrims in Example 4 above (i.e., 42.5% and 40% by weight, respectively). These samples were tested both for ring delamination and for ring strength (dry, wet, and warm wet) in accordance with the procedures set forth herein. The results are tabulated below in Table IV.

In this Example 6, resin-coated Samples were prepared in accordance with the procedure and parameters of Example 4 where the ECG fiberglass yarn was employed in Samples 15-19 and the ECDE fiberglass yarn was employed in Samples 20-24. (Samples 15 and 20 were control samples prepared in the same fashion as Control Samples 1 and 3 of Example 4 and were not

TABLE IV

| Sample | Force Between Rollers (newtons) | Ring Delamination Strength (newtons/cm) | Dry Strength (newtons/cm) | Wet Strength (newtons/cm) | Warm wet Strength (newtons/cm) |
|---|---|---|---|---|---|
| 5 | 0 | 4.0 | 74.3 | 37.7 | 10.7 |
| 6 | 300 | 8.4 | 86.7 | 47.8 | 15.9 |
| 7 | 450 | 9.2 | 92.6 | 48.9 | 14.9 |
| 8 | 600 | 11.8 | 99.2 | 46.1 | 15.4 |
| 9 | 750 | 12.0 | 96.0 | 46.9 | 14.5 |
| 10 | 0 | 8.0 | 85.7 | 35.6 | 12.3 |
| 11 | 300 | 11.1 | 106.7 | 54.2 | 16.2 |
| 12 | 450 | 13.1 | 107.5 | 49.6 | 17.0 |
| 13 | 600 | 15.5 | 108.5 | 56.3 | 18.0 |
| 14 | 750 | 11.5 | 100.3 | 46.6 | 16.7 |

As can be seen with Samples 6-9 and 11-14 which were abraded in accordance with the procedure of FIG. 4 of the present invention, significantly improved ring delamination strength was achieved over the respective Control Samples 5 and 10, with a maximum delamination strength appearing when a force of about 600 to 750 newtons was employed between the knurled roller and the motor driven roller.

As also seen in Table IV, using the presently most preferred method of preparing projections in accordance with the present invention as outlined in FIG. 4, even better dry, wet, and warm wet strengths were achieved than with the unabraded materials. This is surprising in that one would normally expect abrasion to somewhat weaken the integrity of the fabric. However, because of the increased contact between adjacent layers of the material achieved by the present invention and the mechanical interaction between projections and the resin thereon, these surprisingly good strengths are achieved in this presently most preferred embodiment.

abraded in accordance with the process of FIG. 4.) Samples 16-19 and 21-24 were abraded using the procedure of FIG. 4 as set forth in Example 4 above, only using a force of about 450 newtons between the knurled roller and the motor driven roller.

After resin coating in accordance with Example 4, each jumbo roll sample was converted into 4 yard rolls, and the materials were tested for ring delamination strength, dry strength, wet strength, and warm wet strength, and the effect of changing the deflection of the rubbing roller from 2 to 8 millimeters was observed in comparison to the control samples. The ring delamination strengths, dry strengths, wet strengths, and warm wet strengths observed for each of these samples at various rubbing deflections are set forth in Table V below.

TABLE V

| Sample | Rubbing Deflection Distance (mm) | Ring Delamination Strength (newtons/cm) | Dry Strength (newtons/cm) | Wet Strength (newtons/cm) | Warm Wet Strength (newtons/cm) |
|---|---|---|---|---|---|
| 15 | 0 | 8.7 | 84.6 | 35.0 | 11.3 |
| 16 | 2 | 9.6 | 102.2 | 43.9 | 17.4 |
| 17 | 4 | 11.8 | 101.9 | 44.3 | 15.5 |
| 18 | 6 | 10.6 | 94.2 | 45.1 | 15.3 |
| 19 | 8 | 11.6 | 99.1 | 47.4 | 14.2 |
| 20 | 0 | 8.7 | 84.6 | 35.0 | 11.3 |
| 21 | 2 | 11.1 | 91.6 | 40.9 | 11.9 |
| 22 | 4 | 11.5 | 91.6 | 41.6 | 11.9 |
| 23 | 6 | 10.8 | 86.3 | 39.7 | 10.8 |
| 24 | 8 | 11.0 | 89.3 | 33.7 | 11.1 |

For purposes of ring delamination strength, a deflection distance of about 4 millimeters appeared to be best for the samples tested. However, it should be understood that the preferred deflection distance may vary according to the resin-coated materials involved.

EXAMPLE 6

In this example, the effects of the rubbing pressure or force between adjustable rubbing roller 60 and the countercurrently passing abraded scrim surfaces 52 (shown in FIGS. 4 and 5) was tested. The amount of force is referred to in terms of "roller deflection" of adjustable rubbing roller 60. This term refers to the distance rubbing roller 60 displaces scrim 52 extending between idler rollers 62 and 64 from a perfectly vertical position, and hence is related to the pressure between the countercurrently passing scrims.

EXAMPLE 7

In this example, projections within the scope of the present invention were formed along a scrim in accordance with Example 4 using the presently most preferred method of FIG. 4, with the following exceptions. In this Example 7, ECDE-75 1/0 1.0Z yarn was knit into a Scotchflex ® scrim pattern as disclosed herein (instead of the Scotchcast ® 2 scrim pattern used in Example 4), and a force of about 300 newtons was employed between knurled roller 54 and motor driven roller 56 (instead of 750 newtons as in Example 4). All other conditions and parameters for forming projections along a scrim were the same in this Example 7 as for Example 4.

A control scrim using the same yarn was knitted into the Scotchflex® scrim pattern but was not abraded using the process of FIG. 4. Both the abraded scrim of this Example 7 and the control scrim were then coated with the resin described in Example 3 at a coating weight of about 44%. Sample rolls of these casting tapes were then stored in foil pouches for about 5 days at about 20° C. After such time, the resin-coated tapes were removed from their respective pouches and tested according to the procedure set forth herein for ring delamination strength. The ring delamination strength of the abraded resin-coated scrim of this Example 7 was 10.2 newtons/cm while the ring delamination strength observed for the control or nonabraded resin-coated scrim was about 8.0 newtons/cm.

NONORTHOPEDIC APPLICATIONS OF THE PRESENT INVENTION

As mentioned previously, although the resin-coated materials of the present invention have exceptional coated materials also have a wide variety of other utilities and nonorthopedic uses.

For example, the resin-coated materials of the present invention may be used as a protective material to protect the surface of an article or structure from abrasion or corrosion. By way of example only, the resin-coated materials of the present invention may be placed on various structures which are exposed to salt water, for example, oil rigs and ships, so as to protect the underlying structure from salt water corrosion. Similarly, the resin-coated materials may be used on the surfaces of articles or structures which are subject to wear or abrasion. Again, by way of example only, the resin-coated materials may be used to protect dock pilings or other support structures of a dock from abrasion or wear caused by boats butting up against the dock. As a further example, the resin-coated materials may be used to wrap a utility pole or tree so as to prevent rodents from chewing or otherwise damaging the structure of the utility pole or tree.

It will be appreciated that the foregoing examples are merely illustrative, and are not to be considered as comprehensive or in any way limiting. Indeed, the resin-coated materials of the present invention may be used to protect the surface of virtually any article or structure from abrasion and/or corrosion provided that the resin-coated material is capable of being wrapped around the surface of that article or structure. Advantageously, the improved lamination properties of the resin-coated materials of the present invention are also beneficial in such other nonorthopedic applications.

The resin-coated materials of the present invention also find utility in reinforcing, sealing, or repairing the surface of an article or structure requiring reinforcing, sealing, or repairing. For example, the resin-coated materials of the present invention may be wrapped around a leaky pipe or conduit so as to stop the leak and thereby repair the pipe or conduit. Further, the resin-coated materials may be wrapped around the surface of an article to provide a water-tight seal therearound. In addition, the resin-coated materials may be used to join or couple two conduits or objects together. Moreover, the resin-coated materials of the present invention may be used to reinforce or repair conduits carrying fluids, telecommunications conduits, or electrical conduits. Additionally, the resin-coated materials may be used to reinforce or repair cracked articles, such as the handle of a tool or implement.

Again, it will be appreciated that the foregoing examples are not in any way comprehensive or limiting, and that the resin-coated materials of the present invention may be used to reinforce, seal, or repair virtually any article or structure around which the resin-coated materials may be applied. Again, the enhanced lamination properties of the present invention are typically of great benefit in these other nonorthopedic applications.

A more detailed description of nonorthopedic applications of resin-coated materials (which non-orthopedic applications are also possible using the resin-coated materials of the present invention) may be found, for example, in U.S. patent application Ser. No. 343,432, filed Apr. 26, 1989, now abandoned, (which application is a continuation of U.S. application Ser. No. 009,704, filed Feb. 2, 1987, now abandoned, which is a continuation-in-part of U.S. patent application Ser. No. 784,671, filed Oct. 4, 1985 (now U.S. Pat. No. 4,667,661)), incorporated herein by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An article, comprising:
    a knitted or woven fiberglass fabric having on at least one side thereof a plurality of projections, each said projection comprising a bundle of at least about 8 filaments, said side of said fabric having from about 75 to about 1500 projections per gram of fabric; and
    a curable resin coasted onto said fabric;
    wherein said projections on said resin-coated fabric serve to enhance lamination between adjacent layers of the resin-coated fabric when applied around a substrate.

2. An article as defined in claim 1 wherein said side of said fabric has from about 100 to about 1000 projections per gram of fabric.

3. An article as defined in claim 1 wherein said side of said fabric has from about 1 to about 50 projections per square centimeter.

4. An article as defined in claim 1 wherein most of said projections point in substantially the same direction, away from the plane defined by said fabric.

5. An article as defined in claim 1 wherein the average length of each said projection is from about 0.1 to about 16 millimeters.

6. An article as defined in claim 1 wherein the average diameter of each said projection is from about 0.035 to about 2 millimeters.

7. An article as defined in claim 1 wherein said curable resin comprises a water curable, isocyanate functional, polyurethane prepolymer.

8. An article as defined in claim 1 further comprising a storage package within which said curable resin-coated fabric is stored prior to use.

9. An orthopedic casting material, comprising:
    a knitted or woven fiberglass fabric having on at least one side thereof a plurality of projections, each said projection comprising a bundle of at least about 8 filaments, said side of said fabric having from about 75 to about 1500 projections per gram of fabric; and a curable resin coated onto said fabric;

wherein said projections on said resin-coated fabric serve to enhance lamination between adjacent layers of the resin-coated fabric when applied around a body part.

10. An orthopedic casting material as defined in claim 9 wherein each said projection comprises a bundle of from about 8 to about 200 filaments.

11. An orthopedic casting material as defined in claim 9 wherein each said projection comprises a bundle of from about 8 to about 100 filaments.

12. An orthopedic casting material as defined in claim 9 wherein said side of said fabric has from about 100 to about 1000 projections per gram of fabric.

13. An orthopedic casting material as defined in claim 9 wherein said side of said fabric has from about 300 to about 700 projections per gram of fabric.

14. An orthopedic casting material as defined in claim 9 wherein said side of said fabric has from about 1 to about 50 projections per square centimeter.

15. An orthopedic casting material as defined in claim 9 wherein said side of said fabric has from about 5 to about 35 projections per square centimeter.

16. An orthopedic casting material as defined in claim 9 wherein said fabric comprises a knitted fiberglass fabric.

17. An orthopedic casting material as defined in claim 16 wherein said fabric comprises an extensible, heat-set, knitted fiberglass fabric.

18. An orthopedic casting material as defined in claim 9 wherein said fabric comprises a knitted fabric having a plurality of yarns, each said yarn comprising a plurality of filaments, and wherein said projections are formed by breaking at least a portion of the filaments in some of said yarns.

19. An orthopedic casting material as defined in claim 9 wherein the average length of each said projection is from about 0.1 to about 16 millimeters.

20. An orthopedic casting material as defined in claim 9 wherein the average length of each said projection is from about 0.1 to about 8 millimeters.

21. An orthopedic casting material as defined in claim 9 wherein the average diameter of each said projection is from about 0.035 to about 2 millimeters.

22. An orthopedic casting material as defined in claim 9 wherein the modulus of elasticity of said fabric is from about 5 to about 150 gigapascals.

23. An orthopedic casting material as defined in claim 18 wherein from about 0.5% to about 50% of the filaments are broken in those yarns from which said projections are formed.

24. An orthopedic casting material as defined in claim 9 wherein said fabric has a yarn tensile strength of from about 1 to about 2.5 gigapascals.

25. An orthopedic casting material as defined in claim 9 wherein, upon curing said resin-coated fabric, said cured resin-coated fabric has a delamination strength of at least about 9 newtons/cm.

26. An orthopedic casting material as defined in claim 9 wherein most of said projections point in substantially the same direction, away from the plane defined by said fabric.

27. An orthopedic casting material as defined in claim 9 wherein said fabric has projections on both sides thereof.

28. An orthopedic casting material as defined in claim 9 wherein said curable resin comprises a water curable resin.

29. An orthopedic casting material as defined in claim 28 wherein said water curable resin comprises an isocyanate functional, polyurethane prepolymer.

30. An orthopedic casting material as defined in claim 9 further comprising a storage package within which said curable resin-coated fabric is stored prior to use.

31. An article as defined in claim 1 wherein each said projection comprises a bundle of from about 8 to about 200 filaments.

32. An orthopedic casting material, comprising:

a knitted fiberglass fabric having on at least one side thereof a plurality of projections, each said projection comprising a bundle of at least 8 filaments, said side of said fabric sheet having from about 1 to about 50 projections per square centimeter; and a curable resin coated onto said fiberglass fabric.

33. An orthopedic casting material as defined in claim 32 wherein each said projection comprises a bundle of from about 8 to about 200 filaments and wherein said side of said fiberglass fabric has from about 100 to about 1000 projections per gram of fiberglass.

34. An orthopedic casting material as defined in claim 32 wherein each said projection comprises a bundle of from about 8 to about 100 filaments and wherein said side of said fiberglass fabric has from about 300 to about 700 projections per gram of fiberglass.

35. An orthopedic casting material as defined in claim 32 further comprising a storage package within which said curable resin-coated fabric is stored prior to use.

* * * * *

UNITED STATES PATENT AND TRADEMARK OFFICE
CERTIFICATE OF CORRECTION

PATENT NO. : 5,273,802

DATED : December 28, 1993

INVENTOR(S) : Matthew T. Scholz

It is certified that error appears in the above-indentified patent and that said Letters Patent is hereby corrected as shown below:

On the title page, item [75] Inventors:
Delete the names of Ralph A. Wilkens, Robert L. Assell, and Charles E. Alexson as inventors.
Col. 12, line 9, after the second occurrence of "about", insert --4%--.
Col. 12, line 21, after the second occurrence of "about", insert --1%--.
Col. 13, line 24, "no" should be --now--.
Col. 17, line 15, "fiber" should be --fibers--.
Col. 21, line 6, "hen" should be --then--.
Col. 22, line 23, "cm³" should be --cm²--.
Col. 23, line 59, after "sample" insert --was--.
Col. 24, line 40, before the first occurrence of "filaments", insert --7--.
Col. 28, line 1, after "Samples" insert --15-24--.
Col. 29, line 24, before "coated" insert --utility as orthopedic casting materials, these resin- --.
Col. 30, line 40; claim 1, line 7, "coasted" should be --coated--.
Col. 32, line 34; claim 32, line 4, after "least" insert --about--.

Signed and Sealed this

Twenty-eighth Day of June, 1994

Attest:

BRUCE LEHMAN

*Attesting Officer*   *Commissioner of Patents and Trademarks*